(12) United States Patent
Durcan

(10) Patent No.: US 6,491,711 B1
(45) Date of Patent: Dec. 10, 2002

(54) BALLOON CATHETER WITH NON-CIRCULAR BALLOON TAPER AND METHOD OF USE

(75) Inventor: Jonathan P. Durcan, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/712,994

(22) Filed: Nov. 14, 2000

(51) Int. Cl.[7] .............................................. A61M 29/00
(52) U.S. Cl. ...................................... 606/194; 623/1.11
(58) Field of Search ................................. 606/194, 191, 606/192, 108; 623/1.11; 604/103.14, 96

(56) References Cited

U.S. PATENT DOCUMENTS

| | | | |
|---|---|---|---|
| 5,037,392 A | 8/1991 | Hillstead | 604/96 |
| 5,087,246 A * | 2/1992 | Smith | 604/103 |
| 5,163,989 A | 11/1992 | Campbell et al. | 65/110 |
| 5,226,887 A | 7/1993 | Farr et al. | 604/96 |
| 5,456,666 A | 10/1995 | Campbell et al. | 604/96 |
| 6,296,655 B1 * | 10/2001 | Gaudoin et al. | 264/285 |

* cited by examiner

Primary Examiner—Kevin T. Truong
(74) Attorney, Agent, or Firm—Fulwider Patton Lee & Utecht, LLP

(57) ABSTRACT

A balloon catheter including an elongated shaft and a balloon on a digital shaft section having a working section, and tapered sections having an inflated configuration with a non-circular transverse cross section. In one embodiment, the non-circular tapers are triangular, although alternative non-circular cross-sectional designs may be used, such as lobed tapers. The non-circular tapers deflate to form two or more deflated wings along at least a section of the deflated balloon. The deflated wings provide a deflated balloon with a relatively low profile, which facilitates repositioning or removal of the balloon catheter within the patient's vasculature.

20 Claims, 3 Drawing Sheets

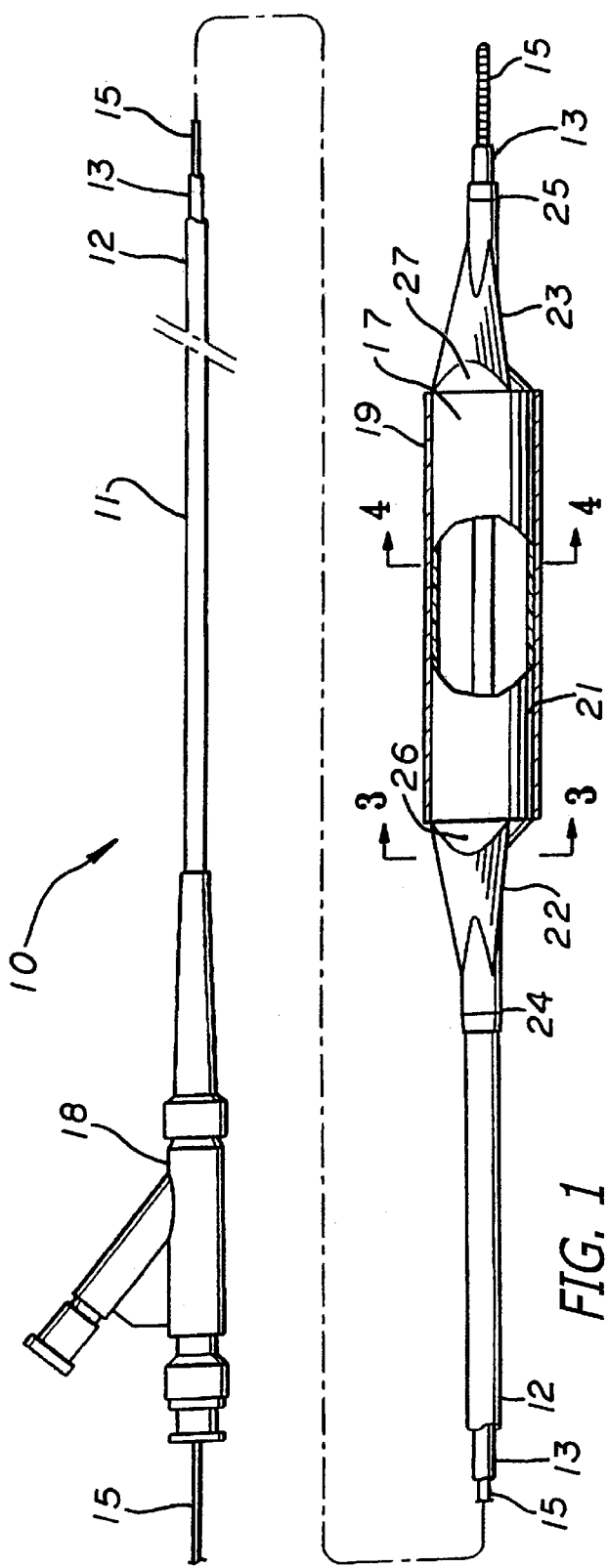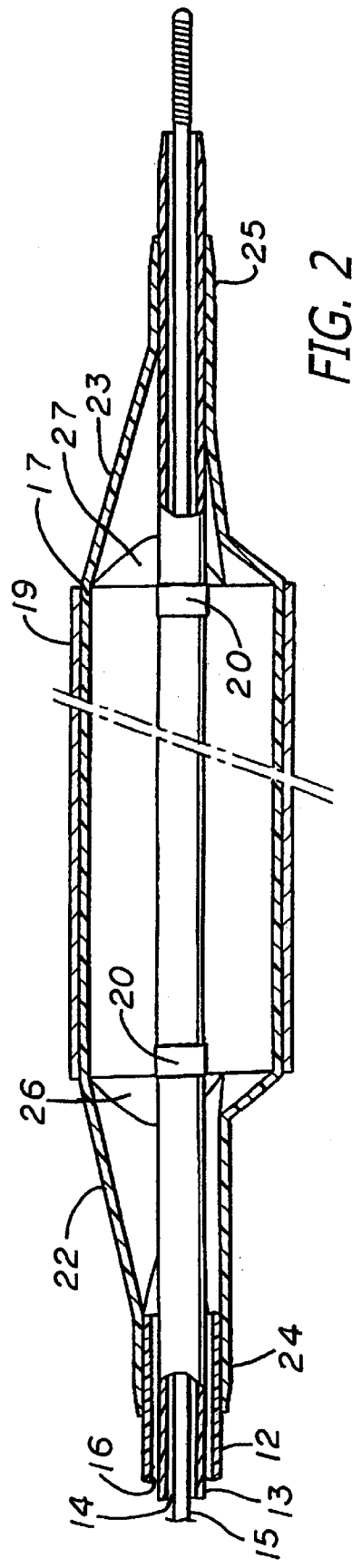

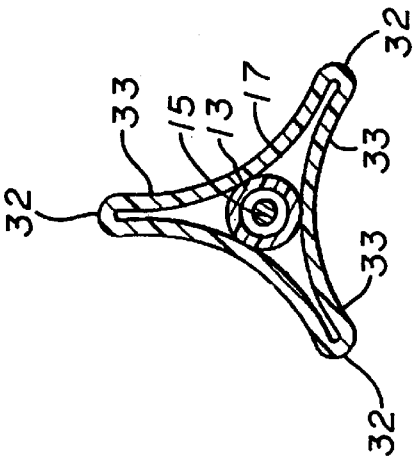
FIG. 6
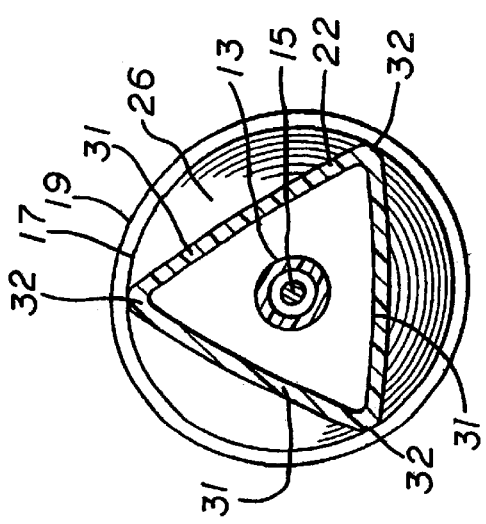
FIG. 4
FIG. 3
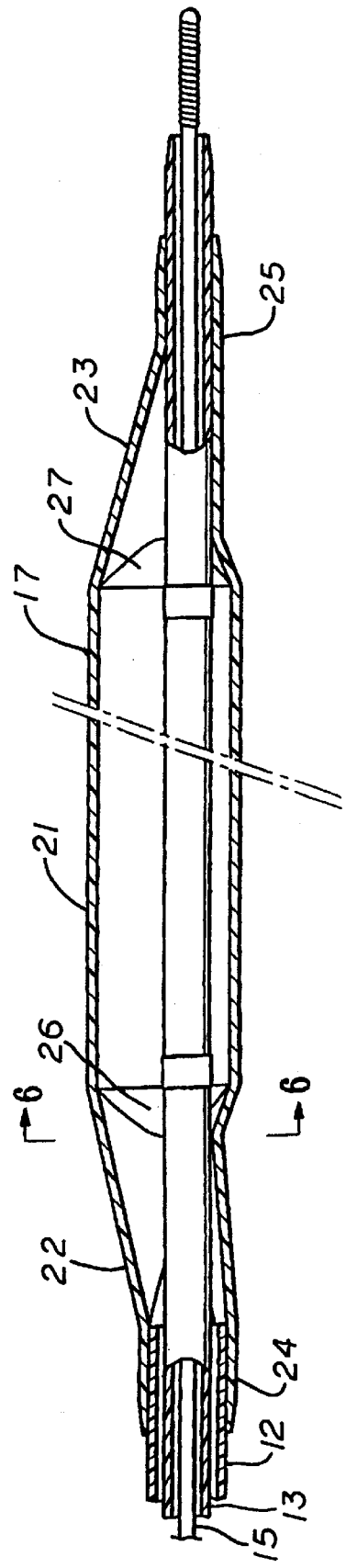
FIG. 5

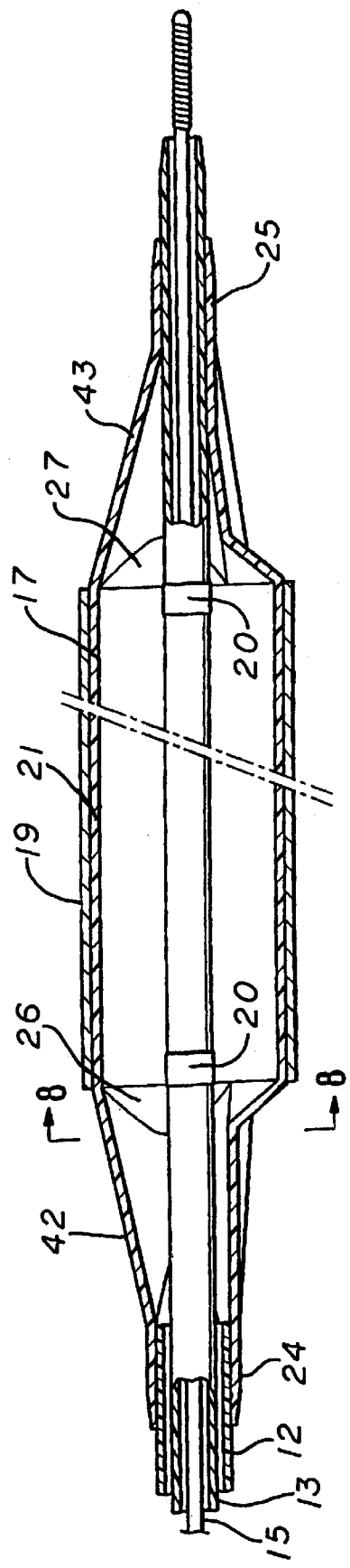
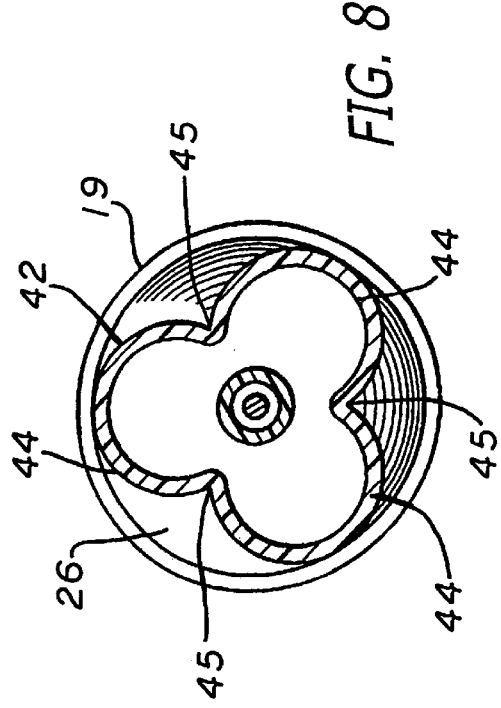
FIG. 7
FIG. 8

BALLOON CATHETER WITH NON-CIRCULAR BALLOON TAPER AND METHOD OF USE

BACKGROUND OF THE INVENTION

This invention relates to the field of medical devices, and more particularly to a catheter balloon having a taper with a non-circular transverse cross section.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter, and the stent is left in place within the artery at the site of the dilated lesion.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy and cross lesions. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range.

In order to decrease the cross sectional profile of the balloon catheter to thereby facilitate advancement of the catheter within the patient's vasculature and across a stenosed region, balloons may be folded into a low profile configuration having balloon wings wrapped around the balloon prior to insertion into the patient. However, one difficulty has been after the balloon is inflated in the patient, the balloon tends to deflate to form a large flat wing or a bunched irregular shape. The resulting relatively large profile of the deflated balloon tends to complicate repositioning or removal of the balloon in the vasculature.

It would be a significant advance to provide a catheter balloon with improved refold upon deflation after inflation of the balloon.

SUMMARY OF THE INVENTION

The invention is directed to a balloon catheter including an elongated shaft and a balloon on a distal shaft section having a working section, and tapered sections having an inflated configuration with a non-circular transverse cross section (hereafter "non-circular tapers"). In one embodiment, the noncircular tapers are triangular, although alternative non-circular cross sectional designs may be used, such as lobed tapers. The non-circular tapers deflate to form two or more deflated wings along at least a section of the deflated balloon. The deflated wings provide a deflated balloon with a relatively low profile, which facilitates repositioning or removal of the balloon catheter within the patient's vasculature.

The balloon catheter of the invention generally comprises an elongated shaft having proximal and distal ends and at least an inflation lumen, and a balloon on a distal shaft section having an interior in fluid communication with the inflation lumen. The balloon has a working section which in a presently preferred embodiment has a cylindrical inflated configuration. The balloon working section or length is typically centrally located and is configured to inflate to perform a therapeutic or diagnostic medical procedure such as dilatation of a stenosis, deployment of a stent, or delivery of a medium. A proximal non-circular tapered section is proximal to the working section, and a distal non-circular tapered section is distal to the working section The non-circular tapered section of the balloon has a plurality of side sections and cusps between adjacent side sections. The balloon deflates with a fold along the line of the each cusp, to thereby form a plurality of deflated wings. In a presently preferred embodiment, the tapered section has three cusps to thereby form three deflated wings. However, in alternative embodiments, the tapered section may have two cusps or more than three cusps, depending on the non-circular shape of the tapered section. A tapered section with three cusps, such as in a triangular cross section, is generally preferred over shapes with four or more cusps due to the lower volume and the smaller outer diameter provided by the tri-cusped tapered section.

The non-circular configuration of the tapers provides tapered sections having a reduced volume compared with conventional conical tapered sections. Preferably, the non-circular tapered section has an inflated inner volume which is not greater than about 75% of the inflated inner volume of a conventional conical tapered section. As a result, the balloon of the invention inflates and deflates faster than a balloon having a conical tapered section due to the reduced inner volume of the balloon of. the invention, and without reducing. the inflated outer diameter of the working section.

In one embodiment, the balloon includes a proximal conical tapered section between the working length and at least a portion of the proximal non-circular tapered section, and a distal conical tapered section between. the working length and at least a portion of the distal non-circular tapered section. The conical section preferably slopes away from the working length at a steeper angle than conventional conical tapered sections. The non-circular tapered sections preferably taper at the same angle than conventional conical tapered sections. However, the non-circular tapered sections may taper at a smaller angle than conventional tapers, i.e., a more gradual taper, which, due to the reduced volume of the non-circular configuration, will not: impact the inflation/deflation time of the balloon. The balloon of the invention is configured to minimize contact between the patient's vessel wall and the sections of the balloon beyond either end of the working length.

In one embodiment in which the balloon is preferably formed of a material such as nylon and has noncompliant to semicompliant expansion, the non-circular tapered sections inflate to form non-circular transverse cross sections at any pressure from above atmospheric pressure to the burst pressure of the balloon. In another embodiment in which the balloon is preferably formed of a relatively soft material such as polyether block amides and polyurethanes and has semicompliant to complaint expansion, the non-circular tapered sections inflate to form non-circular transverse cross sections at any pressure within the working pressure range of the balloon. In one embodiment, the tapered sections inflate to the non-circular shape at an inflation pressure of at least about 15 psi (atmospheric pressure) to about 60 psi, and most preferably about 15 psi to about 30 psi. Depending on the material used to form that balloon, the balloon will rupture with the non-circular tapered sections retaining the non-circular shape. In one embodiment, inflated tapered sections retain the non-circular shape over a pressure range of about 15 psi to about 300 psi, and more specifically about 15 psi to about 265 psi.

One embodiment comprises a method of performing a medical procedure generally including positioning within a body lumen a balloon catheter comprising an elongated shaft having a proximal end, a distal end, and an inflation lumen, and a balloon on a distal shaft section having an interior in fluid communication with the inflation lumen, the balloon having a working section having a cylindrical inflated configuration, and a proximal tapered section proximal to the working section and a distal tapered section distal to the working section, the tapered sections having an inflated configuration with a non-circular transverse cross section. The balloon is inflated within the body lumen from an uninflated configuration to the inflated configuration, the inflated non-circular tapered sections having a smaller inflated diameter than the inner diameter of the body lumen so that the non-circular tapered sections do not inflate against a wall defining the body lumen. The balloon is inflated, with the working length in the cylindrical inflated configuration to perform a procedure such as dilatating a lesion or implanting a stent in the patient's blood vessel. The balloon is deflated to a deflated configuration in which the balloon collapses along a line of the cusps of the non-circular tapered sections to form at least two deflated wings in at least a section of the balloon, and preferably in the working section of the deflated balloon. The catheter is repositioned within or removed from the body lumen with the balloon in the deflated configuration.

The balloon of the invention has improved inflation/deflation times due to the lower volume of the. non-circular tapered section compared with a conventional conical tapered section. Additionally, the non-circular tapered section has a smaller inflated profile, which eliminates or reduces contact between the patient's vessel wall and the sections of the balloon proximal and distal to the balloon working length and the resulting damage to the patient's blood vessel caused by inflation of the tapered sections against the blood vessel wall. Moreover, the balloon of the invention has a low profile deflated configuration due to the non-circular tapered section which deflates to form two or more deflated wings along a length of the deflated balloon. These and. other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter which embodies features of the invention, illustrating the balloon in an inflated configuration with tapered sections having a triangular transverse cross sections.

FIG. 2 is an enlarged longitudinal cross sectional view of a distal portion of the balloon catheter shown in FIG. 1, illustrating the balloon in the inflated configuration.

FIG. 3 is a transverse cross sectional view of the balloon shown in FIG. 1, taken along line 3—3.

FIG. 4 is a transverse cross sectional view of the balloon shown in FIG. 1, taken along line 4—4.

FIG. 5 is an enlarged longitudinal cross sectional view of the distal portion of the balloon catheter shown in FIG. 1, illustrating the balloon in a deflated configuration.

FIG. 6 is a transverse cross sectional view of the balloon shown in FIG. 5, taken along line 6—6, illustrating the deflated balloon wings.

FIG. 7 is a longitudinal cross sectional view of an alternative configuration of a balloon catheter which embodies features of the invention, having a balloon with lobed tapered sections, illustrating the balloon in an inflated configuration.

FIG. 8 is a transverse cross sectional view of the balloon shown in FIG. 7, taken along line 8—8, illustrating the proximal lobed tapered section.

DETAILED DESCRIPTION OF THE INVENTION

FIG. 1 illustrates a balloon catheter 10 which embodies features of the invention. Catheter 10 generally comprises an elongated catheter shaft 11 having an outer tubular member 12 and an inner tubular member 13 disposed within outer tubular member 12. Inner tubular member 13 defines a guidewire lumen 14 adapted to slidingly receive a guidewire 15. The coaxial relationship between outer tubular member 12 and inner tubular member 13 defines annular inflation lumen 16. An inflatable balloon 17 is disposed on a distal section of catheter shaft 11, having a proximal end sealingly secured to the: distal end of outer tubular member 12 and a distal end sealingly secured to the distal end of inner tubular member. 13 so that its interior is in fluid communication with inflation lumen 16. An adapter 18 at the proximal end of catheter shaft 11 is configured to direct inflation fluid into inflation lumen 16 and provide access to guidewire lumen 14. Radiopaque markers 20 on the inner tubular member 13 may be used in positioning the balloon 17 at the desired location in the patient's body lumen. In the embodiment of FIG. 1, a stent 19 is disposed about the working length of the balloon 17.

FIG. 1 illustrates balloon 17 in an inflated configuration. The inflated configuration may be formed at an inflation pressure within the working pressure range of the balloon. Balloon 17 has a working length 21, and a proximal tapered section 22 with a non-circular transverse cross section, and a distal tapered section 23 with a non-circular transverse cross section. FIG. 2 illustrates an enlarged longitudinal cross section of a distal portion of the balloon catheter shown in FIG. 1. As best illustrated in FIG. 3, showing a transverse cross section of the balloon catheter shown in FIG. 1, taken along line 3—3, the proximal and distal tapered sections 22/23 have a triangular transverse cross section (hereafter "triangular tapered sections"). As shown in FIG. 4, illustrating a transverse cross sectional view of the balloon catheter shown in, FIG. 1 taken along lines 4—4, the working length 21 of the balloon inflates to a cylindrical cross section.

The balloon includes a proximal shaft section 24 disposed about and secured to the outer tubular member 12, and a distal shaft section 25 disposed about and secured to the inner tubular member 13. In the embodiment illustrated in FIG. 1, the triangular tapered sections 22/23 are directly adjacent to the respective shaft sections 24/25, and the shaft sections 24/25 are cylindrical. In the embodiment illustrated in FIG. 1, the balloon includes a proximal conical tapered section 26 between the proximal triangular tapered section 22 and the working length 21, and a distal conical tapered section 27 between the distal triangular tapered section 23 and the working length 21. However, in alternative embodiments (not shown) one or both of the conical sections 26/27 may be omitted, and the balloon provided with a stepped working length. For example, in one embodiment (not shown), the triangular tapered sections 22/23 are adjacent to proximal and distal cylindrical sections similar to the working length, having an abrupt, substantially perpendicular transition from the working length 21 to the proximal and distal cylindrical sections. The conical sections 26/27 have a relatively short length, preferably about 10% to about 30%, most preferably about 15% to about 25% of the length of the triangular non-circular tapered sections 22/23. The conical-sections 26/27 taper away from the working length at an angle of about 30° to about 60°, preferably about 40° to about 50°. In a presently preferred embodiment, the angle and length of the proximal conical section 26 is the same as the angle and length of the distal conical section 27. The non-circular triangular tapered sections taper at an angle of about 15° to about 30°, preferably about 20° to about 25°. In one embodiment, the angle of the non-circular triangular tapered sections 22/23 is about 25% to about 75% of the angle of the conical sections 26/27. In a presently preferred embodiment, the angle and length of the proximal triangular tapered section 22 is the same as the angle and length of the distal triangular tapered section 23.

As best illustrated in FIG. 3, the non-circular triangular tapered sections 22/23 each have three side sections 31 separated by cusp sections 32. In the embodiment illustrated in FIG. 1, each cusp section extends along the length of the tapered side section in a line longitudinally aligned with the longitudinal axis of the balloon 17. However, in an alternative embodiment (not shown), the cusps do not extend longitudinally aligned with the balloon longitudinal axis, for example where the cusps extends circumferencially around the tapered section. The non-circular triangular tapered sections 22/23 have a smaller inflated outer diameter and thus a smaller inflated inner volume than would otherwise be provided by conventional conical tapered sections. Preferably, the triangular tapered section 22 or 23 defines an inflated inner volume of about 40% to about 75%, most preferably about 50% to about 60% of the inflated inner volume of a conventional conical tapered section having the same length.

In one embodiment, the non-circular triangular tapered sections 22/23 deflate with a fold along the line of each cusp section 32, so that the side sections 31 collapse in around the cusp sections 32 to form three deflated wings 33 (FIG. 6). FIG. 5 illustrates a longitudinal cross sectional view of the balloon shown in FIG. 2, with the balloon in a deflated configuration. FIG. 6 illustrates a transverse cross section of the balloon shown in FIG. 5, taken along line 6—6, illustrating the three deflated wings 33. As the balloon 17 is deflated, the deflated shape of the triangular tapered sections having three wings forces the working length of the balloon to also deflate into the tri-winged configuration shown in FIG. 6. In one embodiment, the triangular tapered section's 22/23 have cusps 32 which are thicker and therefore more rigid than the side sections 31. A balloon 17 having a non-circular tapered section different from the triangular tapered section and with more or less than three cusp sections 32 will deflate similar to the balloon illustrated in FIG. 6 but with more or less than the three wings 33 illustrated in FIG. 6. To form the deflated configuration, the physician typically removes the inflation fluid in the balloon 17 by drawing the fluid out with a syringe. A vacuum may be applied to further collapse the balloon. In the deflated configuration, catheter 10 may be repositioned or removed from the patient's body lumen, which typically involves withdrawing the catheter 10 into a guiding catheter (not shown), and wings 33 provide a low profile configuration that facilitates this procedure.

Inflation of the balloon 17 expands the stent 19 mounted thereon for implanting the stent within the patient's body lumen. The-balloon 17 can be deflated, leaving the expanded stent 19 implanted in place within the body lumen. In a presently preferred embodiment, the proximal and distal ends of the stent are located at or between the proximal and distal ends of the balloon working length. However, in alternative embodiments the ends of the stent may be beyond the ends of the working length, at the conical sections 26/27, or at the non-circular tapered sections 22/23. Stent 19 would typically be mounted on the working length 21 of the uninflated balloon prior to introduction of the catheter 10 into the patient. The distal end of catheter 10 may be advanced to a desired region of a patient's lumen in a conventional manner, and balloon 17 may be inflated to expand stent 19, seating it in the lumen. The balloon 17 is deflated to form deflated wings 33, and the balloon catheter 10 may be repositioned for another procedure or removed from the body lumen. Although illustrated as a stent deploying balloon catheter in FIG. 1, the balloon catheter of the invention may be used for a variety of suitable applications such as balloon angioplasty, drug delivery, and the like.

FIG. 7 illustrates an alternative embodiment of balloon 17 having noncircular proximal and distal tapered sections 42 and 43. Many of the reference numerals for elements otherwise similar to the embodiment of FIG. 1 are used in FIG. 7. As best illustrated in FIG. 8 showing a transverse cross section of the inflated balloon shown in FIG. 7 taken along line 8—8, the non-circular tapered sections 42/43 have a lobed configuration having three side sections comprising lobes 44 separated by cusp sections 45. During deflation of the balloon 17 illustrated in FIG. 7, the non-circular lobed tapered sections 42/43 deflate with a fold corresponding to a wing tip along the line at the center each lobed side section 44, so that the cusp sections 45 collapse radially inwardly and the walls of a lobed side section 44 collapse together, to form three deflated wings (not shown). As discussed above in relation to the embodiment of FIG. 2, the deflated shape of the lobed tapered sections 42/43 having three wings forces the working length 21 of the balloon to also deflate into the tri-winged configuration. A presently preferred embodiment has three lobed side sections 44, however in alternative embodiments, the balloon may have two lobed side sections 44 or more than three lobed side sections 44. The lobes 44 may have a variety of suitable shapes, such that the lobes preferentially collapse during deflation of the balloon to each form a separate deflated wing. In a presently preferred embodiment, each lobed side section 44 comprises a rounded projecting portion with a curved shape. In an alternative embodiment, each lobed side section 44 has an angled configuration such as a triangular shape. In a presently preferred embodiment, each lobed tapered section 42/43 has three lobed side sections 44, so that the balloon deflates to form three deflated wings.

In the embodiment illustrated in FIG. 8, the lobed tapered sections 42/43 have a smaller inflated outer diameter and thus a smaller inflated inner volume than would otherwise be provided by conventional conical tapered. sections. Preferably, the lobed tapered section 42 or 43 has an inflated inner volume of about 50% to about 75%, most preferably about 60% to about 70% of the inflated inner volume of a conventional conical tapered section having the same length.

In a presently preferred embodiment, the cusp sections 32/45 do not have separate reinforcing members applied thereto. However, in alternative embodiments such reinforcing members, including strips of material, may be present at the cusps. In a presently preferred embodiment, the material forming the balloon is uniform, i.e., side sections and cusp sections of the balloon are not formed of different material. The balloon can be formed from a variety of suitable polymeric materials commonly used to form catheter balloons, including polyamides such as nylon, nylon 12, polyether block amides (PEBAX), polyurethane, polyurethane copolymers such as PELLETHANE, polyesters, and blends thereof.

The balloon 17 of the invention can be formed using a variety of suitable methods, such as blow molding or shaped extrusion. The balloon 17 is typically formed by blow molding a polymeric tube in a balloon mold having an inner surface corresponding to the desired outer surface of the balloon. The polymeric tube is typically expanded in the mold at elevated pressure and temperature, and optionally under axially tension, to form the balloon. The balloon may optionally be subjected to heat treatments at elevated temperatures in the mold. The balloon is removed from the mold and mounted on the catheter shaft 11. The uninflated configuration of the balloon typically has wings which are folded around the balloon to form a low profile configuration prior to introduction and advancement within the body lumen. In a presently preferred embodiment, the balloon is heat set in the folded configuration prior to use, which may improve the refold of the balloon, by subjecting the folded balloon to elevated temperatures of about 100° F. to about 150° F. for about 5 to about 15 seconds, depending on the balloon material. The folded balloon is preferably pressed during the heat setting, by applying a radially inward pressure on an outer surface of the balloon around the circumference of the balloon, which may reduce the profile of the folded balloon. In the embodiment having a stent mounted on the balloon for deployment in a body lumen, in order to firmly mount the stent on the balloon, the stent is placed onto the folded balloon, a restraining sheath is placed therearound, and the balloon is then pressurized and heated to about 150° F. to about 230° F. for about 30 to about 90 seconds while being restrained from expanding by the sheath.

A method of performing a medical procedure comprises positioning within a body lumen a balloon catheter comprising an elongated shaft having a proximal end, a distal end, and an inflation lumen, and a balloon on a distal shaft section having an interior in fluid communication with the inflation lumen, and having a working section having a cylindrical inflated configuration, and a proximal tapered section proximal to the working section and a distal tapered section distal to the working section, the tapered sections having an inflated configuration with a non-circular transverse cross section. The non-circular tapered sections comprises cusps separated by side sections. The balloon is inflated within the body lumen from an uninflated configuration to the inflated configuration, the inflated non-circular tapered sections having a smaller inflated diameter than the inner diameter of the body lumen so that at least the side sections of the non-circular tapered sections do not inflate against a vessel wall defining the body lumen. The balloon is inflated, with the working length in the cylindrical inflated configuration to perform a procedure such as dilatating a lesion or implanting a stent in the patient's blood vessel. The balloon is deflated to a deflated configuration and the catheter is repositioned within or removed from the body lumen. In one embodiment, deflating the balloon comprises collapsing the balloon along a line of the cusps of the non-circular tapered sections to form at least two, and preferably three deflated wings in the working section of the deflated balloon. The terminology along a line of the cusps should be understood to include the embodiment of FIG. 1 in which the cusps in the deflated balloon form a fold at the outer tip of the wing, and the embodiment of FIG. 7 in which the cusps in the deflated balloon form a fold at the base of the wing between adjacent wings.

The dimensions of catheter 10 are determined largely by the size of the guidewires to be employed and the size of the artery or other body lumen through which the catheter must pass or the size of the stent being delivered. Typically, the outer tubular member 16 has an outer diameter of about 0.02 to about 0.04 inch (0.05 to 0.10 cm), usually about 0.037 inch (0.094 cm), an inner diameter of about 0.015 to about 0.035 inch (0.038 to 0.089 cm), usually about 0.03 inch (0.076 cm). The wall thickness of the outer tubular member 16 can vary from about 0.002 to about 0.008 inch (0.0051 to 0.0201 cm), typically about 0.003 inch (0.0076 cm). The inner tubular member 13 typically has an outer diameter of about to about 0.019 inch to about 0.023 inch (0.048 to 0.058 cm), usually about 0.021 inch (0.053 cm). The overall working length of the catheter 10 may range from about 100 to about 150 cm, and is typically about 140 cm. Preferably, balloon 17 may have a total length about 2 cm to about 5 cm and preferably about 3 cm, a working section length of about 1 to about 4 cm and preferably about 2 cm, and an inflated working outer diameter of about 1 to about 8 mm, preferably about 2 to about 5 mm within a working pressure range of the balloon. The non-circular tapered sections have a length of about 0.2 to about 1.6 cm, preferably about 0.3 to about 0.7 cm, and an inflated outer diameter at a center point along the length of the section, and at its maximum dimension (i.e., from a cusp to the opposite side section), of about 0.3 mm to about 6 mm, preferably about 1 to about 3 mm.

The balloon catheter illustrated in FIG. 1 is an over-the-wire catheter. However, various balloon catheter designs may be used, such as rapid exchange and fixed wire catheters. Rapid exchange catheters typically have an elongated shaft with a proximal end, a distal end with a balloon on a distal shaft section in fluid communication with an inflation lumen, a distal port in the distal end of the catheter, a proximal port spaced a substantial distance from the proximal end of the catheter closer to the distal end than to the proximal end, and a short guidewire lumen extending between the proximal and distal ports.

The invention has been discussed in terms of certain preferred embodiments. One of skill in the art will recognize that various modifications may be. made without departing from the scope of the invention. For example, while the balloon of the invention has been discussed primarily in terms of an embodiment having a proximal and a distal tapered section with a non-circular transverse cross section, the balloon may have only one non-circular tapered section. Moreover, while certain features may be shown or discussed in relation to a particular embodiment, such individual features may be used on the various other embodiments of the invention.

What is claimed is:

1. A balloon catheter, comprising
   a) an elongated shaft having a proximal end, a distal end, and an inflation lumen; and
   b) a balloon on a distal shaft section having an interior in fluid communication with the inflation lumen, a working section with a cylindrical inflated configuration, a proximal tapered section proximal to the working section, and a distal tapered section distal to the working section, the proximal and distal tapered sections having an inflated configuration with a non-circular transverse cross section.

2. The balloon catheter of claim 1 wherein the non-circular tapered sections have a triangular transverse cross section.

3. The balloon catheter of claim 1 wherein the non-circular tapered sections have a lobed transverse cross section.

4. The balloon catheter of claim 3 wherein each of the, proximal and distal non-circular tapered sections have 2 or more lobes.

5. The balloon catheter of claim 3 wherein each lobe forms a deflated balloon wing.

6. The balloon of claim 1, wherein the balloon includes a proximal conical tapered section between the working section and at least a portion of the proximal non-circular tapered section, and a distal conical tapered section between the working section and at least a portion of the distal non-circular tapered section.

7. The balloon catheter of claim 6 wherein the proximal conical tapered section tapers at a first angle, and the proximal non-circular tapered section tapers at a second angle less than the first angle.

8. The balloon catheter of claim 6, wherein the conical tapered sections taper at an angle of about 30° to about 60°.

9. The balloon catheter of claim 8 wherein the non-circular tapered sections taper at an angle of about 15° to about 30°.

10. The balloon catheter of claim 1 wherein the inflated configuration is at a pressure within-a working pressure range of the balloon.

11. The balloon catheter of claim 9, wherein the inflated configuration is at a pressure of about 15 psi to about 300 psi.

12. The balloon catheter of claim 1 wherein the balloon has a deflated configuration with at least two wings in the working section.

13. The balloon catheter of claim 1 wherein the balloon has a deflated configuration with three wings in each of the proximal and distal tapered sections.

14. The balloon catheter of claim 13 wherein the three wings extend within the working section of the deflated balloon.

15. The balloon catheter of claim 1 wherein a material forming the working section and tapered sections of the balloon is the same around a circumference of the balloon.

16. The balloon catheter of claim 1 wherein the balloon includes a proximal shaft section at a proximal end of the proximal non-circular tapered section, and a distal shaft section at a distal end of the distal non-circular tapered section, the balloon shaft sections being secured to the elongated shaft.

17. The balloon catheter of claim 1 wherein the balloon has a stent disposed about and mounted on at least a portion of the working section.

18. A method of performing a medical procedure, comprising
   a) positioning within a body lumen a balloon catheter, comprising
      i) an elongated shaft having a proximal end, a distal end, and an inflation lumen; and
      ii) a balloon on a distal shaft section having an interior in fluid communication with the inflation lumen, a working section with a cylindrical inflated configuration, a proximal tapered section proximal to the working section, and a distal tapered section distal to the working section, the proximal and distal tapered sections comprising cusps separated by side sections having an inflated configuration with a non-circular transverse cross section; and
   b) inflating the balloon from an uninflated configuration to the inflated configuration within the body lumen, so that at least the side sections of the non-circular tapered sections do not inflate against a wall defining the body lumen; and
   c) deflating the balloon to a deflated configuration.

19. The method of claim 18 wherein deflating the balloon comprises collapsing the balloon along a line of the cusps of the non-circular tapered sections to form at least two deflated wings in at least the working section of the deflated balloon.

20. The method of claim 19 wherein the balloon has a stent mounted thereon, and including inflating the balloon to expand the stent to an expanded cylindrical configuration.

* * * * *

UNITED STATES PATENT AND TRADEMARK OFFICE
CERTIFICATE OF CORRECTION

PATENT NO.   : 6,491,711 B1
DATED        : December 10, 2002
INVENTOR(S)  : Jonathan P. Durcan It is certified that error appears in the above-identified patent and that said Letters Patent is hereby corrected as shown below:

Column 10,
Line 1, change "9", to read -- 10 --.

Signed and Sealed this

Twenty-seventh Day of May, 2003

JAMES E. ROGAN
*Director of the United States Patent and Trademark Office*